US012714364B2

(12) United States Patent
Theodore et al.

(10) Patent No.: US 12,714,364 B2
(45) Date of Patent: Aug. 25, 2026

(54) MONITORING AND TREATMENT OF INJURIES USING WEARABLE DEVICES

(71) Applicant: THE JOHNS HOPKINS UNIVERSITY, Baltimore, MD (US)

(72) Inventors: Nicholas Theodore, Ruxton, MD (US); Amir Manbachi, Baltimore, MD (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 495 days.

(21) Appl. No.: 18/247,760

(22) PCT Filed: Oct. 6, 2021

(86) PCT No.: PCT/US2021/053699
§ 371 (c)(1),
(2) Date: Apr. 4, 2023

(87) PCT Pub. No.: WO2022/076510
PCT Pub. Date: Apr. 14, 2022

(65) Prior Publication Data

US 2023/0363711 A1 Nov. 16, 2023

Related U.S. Application Data

(60) Provisional application No. 63/088,310, filed on Oct. 6, 2020.

(51) Int. Cl.
*A61B 5/00* (2006.01)
*A61B 5/01* (2006.01)
(Continued)

(52) U.S. Cl.
CPC ............ *A61B 5/681* (2013.01); *A61B 5/0036* (2018.08); *A61B 5/01* (2013.01); *A61B 5/021* (2013.01);
(Continued)

(58) Field of Classification Search
CPC .. A61B 5/01; A61B 5/204; A61B 8/02; A61B 8/04
See application file for complete search history.

(56) References Cited

U.S. PATENT DOCUMENTS 6,210,346 B1 4/2001 Hall et al.
6,730,095 B2 5/2004 Olson et al.
(Continued)

FOREIGN PATENT DOCUMENTS

KR 20020082245 A 10/2002
WO WO-2011097291 A1 * 8/2011 ......... G01N 21/4795
(Continued)

OTHER PUBLICATIONS

Doherty, F. (Authorized officer), International Preliminary Report on Patentability issued in corresponding International Application No. PCT/US2021/053682 mailed on Apr. 20, 2023, 8 pages.
(Continued)

*Primary Examiner* — Brian T Gedeon
(74) *Attorney, Agent, or Firm* — MH2 Technology Law Group LLP

(57) ABSTRACT

A patient monitoring and/or treatment system and method is disclosed. The system includes a wearable device configured to be wearable on an external portion of a patient. The wearable device configured to monitor and/or treat a biological feature of the patient, the wearable device including: one or more ultrasonic transmitters that provide ultrasonic energy to a monitoring site and/or a treatment site of the patient; one or more ultrasonic receivers that receive reflected ultrasonic energy from the monitoring site and/or the treatment site; and a controller that controls the one or more ultrasonic transmitter and the one or more ultrasonic receivers and determines an attribute of the biological fea-
(Continued)

ture based on the ultrasonic energy that is provided and the ultrasonic energy that is received.

20 Claims, 11 Drawing Sheets

(51) Int. Cl.

| | |
|---|---|
| ***A61B 5/021*** | (2006.01) |
| ***A61B 5/20*** | (2006.01) |
| ***A61B 5/24*** | (2021.01) |
| ***A61B 5/389*** | (2021.01) |
| ***A61B 8/00*** | (2006.01) |
| ***A61B 8/02*** | (2006.01) |
| ***A61B 8/04*** | (2006.01) |
| ***A61B 8/08*** | (2006.01) |
| ***A61M 27/00*** | (2006.01) |
| ***A61N 1/04*** | (2006.01) |
| ***A61N 1/36*** | (2006.01) |
| *A61M 25/10* | (2013.01) |

(52) U.S. Cl.

CPC ................ *A61B 5/204* (2013.01); *A61B 5/24* (2021.01); *A61B 5/389* (2021.01); *A61B 5/4566* (2013.01); *A61B 5/486* (2013.01); *A61B 5/6802* (2013.01); *A61B 5/686* (2013.01); *A61B 5/6867* (2013.01); *A61B 8/02* (2013.01); *A61B 8/04* (2013.01); *A61B 8/0808* (2013.01); *A61B 8/4477* (2013.01); *A61B 8/5207* (2013.01); *A61M 27/006* (2013.01); *A61N 1/0476* (2013.01); *A61N 1/36014* (2013.01); *A61N 1/36062* (2017.08); *A61N 1/36135* (2013.01); *A61B 2562/0247* (2013.01); *A61B 2562/0271* (2013.01); *A61M 2025/1052* (2013.01); *A61M 2205/3303* (2013.01); *A61M 2205/3306* (2013.01); *A61M 2205/3334* (2013.01); *A61M 2205/3344* (2013.01); *A61M 2205/3372* (2013.01); *A61M 2205/3523* (2013.01); *A61M 2230/04* (2013.01); *A61M 2230/50* (2013.01)

(56) References Cited

U.S. PATENT DOCUMENTS

| | | | |
|---|---|---|---|
| 8,343,086 | B2 | 1/2013 | Dacey et al. |
| 8,805,542 | B2 | 8/2014 | Tai et al. |
| 8,961,936 | B2 | 2/2015 | Wiley et al. |
| 9,302,112 | B2 | 4/2016 | Bornzin et al. |
| 9,538,957 | B2 | 1/2017 | Malackowski et al. |
| 9,913,585 | B2 | 3/2018 | McCaffrey et al. |
| 11,471,108 | B2 | 10/2022 | Lange et al. |
| 2007/0043591 | A1 | 2/2007 | Meretei et al. |
| 2007/0233079 | A1 | 10/2007 | Fallin et al. |
| 2009/0247899 | A1 | 10/2009 | Dennison et al. |
| 2011/0118567 | A1 | 5/2011 | Roche |
| 2012/0065548 | A1 | 3/2012 | Morgan et al. |
| 2012/0302995 | A1 | 11/2012 | Hochareon |
| 2013/0023814 | A1 | 1/2013 | Bertrand et al. |
| 2013/0102833 | A1 | 4/2013 | John et al. |
| 2014/0276347 | A1 | 9/2014 | Stone |
| 2014/0304773 | A1 | 10/2014 | Woods et al. |
| 2015/0142074 | A1 | 5/2015 | Bar-Yoseph et al. |
| 2015/0321010 | A1 | 11/2015 | Marnfeldt |
| 2016/0140834 | A1 | 5/2016 | Tran |
| 2016/0157769 | A1 | 6/2016 | Min et al. |
| 2016/0339239 | A1 | 11/2016 | Yoo et al. |
| 2016/0341600 | A1* | 11/2016 | Aloe ........................ G01V 8/12 |
| 2017/0123487 | A1 | 5/2017 | Hazra et al. |
| 2017/0266410 | A1 | 9/2017 | Farrell et al. |
| 2018/0056079 | A1 | 3/2018 | Hahn et al. |
| 2019/0167188 | A1 | 6/2019 | Gifford et al. |
| 2019/0269914 | A1* | 9/2019 | Moaddeb ........... A61H 23/0245 |
| 2020/0030099 | A1 | 1/2020 | Sampath et al. |
| 2020/0069247 | A1 | 3/2020 | Hunter |
| 2020/0069943 | A1* | 3/2020 | Campean ........... A61N 1/36021 |
| 2020/0114174 | A1 | 4/2020 | Alam et al. |
| 2020/0229702 | A1 | 7/2020 | Sekowski |
| 2021/0196944 | A1* | 7/2021 | Lin ..................... A61B 8/4236 |
| 2021/0207942 | A1 | 7/2021 | Winkelmann et al. |
| 2022/0176133 | A1 | 6/2022 | Buddha et al. |
| 2022/0266018 | A1 | 8/2022 | Mansell |
| 2023/0371901 | A1 | 11/2023 | Manbachi et al. |
| 2023/0372685 | A1 | 11/2023 | Manbachi et al. |
| 2023/0381504 | A1 | 11/2023 | Yoo et al. |
| 2023/0404473 | A1 | 12/2023 | Theodore et al. |

FOREIGN PATENT DOCUMENTS

| | | | |
|---|---|---|---|
| WO | 2018118673 | A2 | 6/2018 |
| WO | 2018153943 | A1 | 8/2018 |
| WO | 2019073341 | A1 | 4/2019 |
| WO | 2019236254 | A1 | 12/2019 |

OTHER PUBLICATIONS

Doherty, F. (Authorized officer), International Preliminary Report on Patentability issued in corresponding International Application No. PCT/US2021/053684 mailed on Apr. 20, 2023, 7 pages.

Kobayashi, M. (Authorized officer), International Preliminary Report on Patentability issued in corresponding International Application No. PCT/US2021/053738 mailed on Apr. 20, 2023, 8 pages.

Lee, S. (Authorized officer), International Preliminary Report on Patentability issued in corresponding International Application No. PCT/US2021/053699 mailed on Apr. 20, 2023, 6 pages.

Belugin, M. (Authorized officer), International Search Report and Written Opinion in corresponding International Application No. PCT/US2021/053684 mailed on Dec. 29, 2021, 9 pages.

Belugin, M. (Authorized officer), International Search Report and Written Opinion in corresponding International Application No. PCT/US2021/053699 mailed on Dec. 9, 2021, 7 pages.

Belugin, M. (Authorized officer), International Search Report and Written Opinion in corresponding International Application No. PCT/US2021/053738 mailed on Dec. 16, 2021, 10 pages.

Khapsirokov, R. (Authorized officer), International Search Report and Written Opinion in corresponding International Application No. PCT/US2021/053682 mailed on Jan. 13, 2022, 10 pages.

Thomas, S. (Authorized officer), International Search Report and Written Opinion in corresponding International Application No. PCT/US2024/020941 mailed on Jul. 31, 2024, 8 pages.

Non-Final Office Action issued in corresponding U.S. Appl. No. 18/247,759 mailed on Nov. 19, 2025, 56 pages.

Non-Final Office Action issued in corresponding U.S. Appl. No. 18/247,757 mailed on Nov. 7, 2025, 35 pages.

Baharlou, S. (Authorized officer), International Preliminary Report on Patentability in corresponding International Application No. PCT/US2024/020941 mailed on Nov. 20, 2025, 7 pages.

Non-Final Office Action issued in corresponding U.S. Appl. No. 18/247,697 mailed on Feb. 17, 2026, 69 pages.

* cited by examiner 1000
1002
1004
1006
1008
1010

900
902
904
906

800
802
804
806
808

MONITORING AND TREATMENT OF INJURIES USING WEARABLE DEVICES

CROSS-REFERENCE TO RELATED APPLICATIONS

This application is the national stage entry of International Patent Application No. PCT/US2021/053699, filed on Oct. 6, 2021, and published as WO 2022/076510 A1 on Apr. 14, 2022, which claims the benefit of U.S. Provisional Patent Application Ser. No. 63/088,310, filed on Oct. 6, 2020, both of which are hereby incorporated by reference herein in their entireties.

STATEMENT REGARDING FEDERALLY SPONSORED RESEARCH

This invention was made with Government support under N66001-20-2-4075, awarded by Department of the Navy. The Government has certain rights in the invention.

BACKGROUND

Few viable treatment options are available for patients who have suffered a traumatic injury, such as a spinal cord injury (SCI), brain injury, burn injury, or another type of serious injury. Spinal cord injury can be a devastating condition with lifelong complications. Spinal cord injury monitoring and interventions remain in their infancy compared with advances made for other types of injuries. For example, monitoring of intracranial pressure and tissue oxygenation are mainstays in the treatment of acute traumatic brain injury (TBI), and information gathered from this monitoring is also helpful in the prevention and mitigation of secondary injury. Similar to TBI, SCI leads to severed axons, glial scarring, and a global lack of innate regenerative capacity at the injury site during the acute phase. Secondary injury is common due to subsequent ischemia and inflammation, and it leads to further tissue destruction, prolonging recovery.

Disruption of the autonomic nervous system after severe SCI, particularly rostral to thoracic level, where sympathetic nervous system fibers exit the spinal cord and innervate the immune system, leads to dysregulated local and systemic inflammatory responses, impairment of immune function, and increased infection risk, all of which hinder recovery after SCI. Acute inflammation in the spinal cord exacerbates the primary SCI injury, triggers secondary injury, worsens ischemia and scarring, and inhibits recovery. Chronic SCI results in long-term systemic inflammation, which is clinically exacerbated by a state of chronic immunosuppression.

Spinal cord injury and other types of injury are not totally preventable. Prevention and mitigation of the pathophysiologic sequelae of an SCI devastating injury are critical to preserving spinal cord tissue and improving functional outcome after injury. In acute SCI, multimodal real-time monitoring of biomarkers such as perfusion pressure, oxygenation, intrathecal pressure, temperature, and inflammatory markers does not exist. Interventions such as cerebrospinal fluid (CSF) drainage and maintaining mean arterial pressure (MAP) goals have shown great promise. Electrical stimulation has also been reported to influence inflammatory pathways. However, it is currently impossible to optimally titrate these therapies in real-time because there is no way to directly and continuously assess the spinal cord after SCI.

Loss of motor control is perhaps the most obvious sequela of SCI. However, multiple systems, including the functions of cardiovascular and bladder control, are affected after this injury. Urological complications after SCI require lifelong management. SCI also causes profound disruption of the cardiovascular (CV) system, particularly in motor-complete injuries in the cervical and upper thoracic levels. CV dysregulation leads to persistent hypotension, bradycardia, orthostatic hypotension, and episodes of autonomic dysreflexia, which drastically diminish quality of life by affecting overall health and preventing patients from engaging in activities of daily life. Ultimately, the simultaneous restoration of motor, CV, and urologic systems would allow patients with SCI and certain other injuries to fully participate in daily activities.

Accordingly, there is a need for systems and methods for effective monitoring and treatment of spinal cord and other injuries.

SUMMARY

The present disclosure relates, in certain aspects, to methods, devices, systems, and computer readable media of use in monitoring of and treatment of an injury in a human. In certain applications, for example, the injury may be a spinal cord injury. These and other aspects will be apparent upon a complete review of the present disclosure, including the accompanying figures.

In accordance with some aspects, the present disclosure provides a system, device or corresponding method for treatment of an injury in a human. The system may include an implantable device configured to be implanted into a human body, the implantable device having a sensing device and a treatment device, the sensing device configured to sense a first condition of the injury and to generate a signal corresponding to the sensed condition, the treatment device configured to provide treatment to the injury, a wearable device configured to be wearable on an external portion of the human body, the wearable device configured to sense a condition of the human related to the injury, and a controller connected to the implantable device and to the wearable device, the controller configured to receive signals from the implantable device and the wearable device and to control the implantable device to selectively cause the treatment device to apply the treatment based on the signal corresponding to the sensed condition.

In accordance with examples of the present disclosure, a patient monitoring and/or treatment system is disclosed that comprises a wearable device configured to be wearable on an external portion of a patient, the wearable device configured to monitor and/or treat a biological feature of the patient, the wearable device comprising: one or more ultrasonic transmitters that provide ultrasonic energy to a monitoring site and/or a treatment site of the patient; one or more ultrasonic receivers that receive reflected ultrasonic energy from the monitoring site and/or the treatment site; and a controller that controls the one or more ultrasonic transmitter and the one or more ultrasonic receivers and determines an attribute of the biological feature based on the ultrasonic energy that is provided and the ultrasonic energy that is received.

Various additional features can be added in the patient monitoring and/or treatment system including one or more of the following features. The biological feature is a blood pressure, a tissue temperature, a tissue elasticity, or a volume of a target organ. The target organ is a bladder, a liver, a brain, or another organ. The patient monitoring and/or treatment system can further comprise one or more stimulating electrodes that provide therapeutic electrical stimulation to the monitoring site and/or the treatment site; and one or more recording electrodes that provide recording of neural activity at the monitoring site and/or the treatment site, wherein the controller further controls the one or more stimulating electrodes and the one or more recording electrodes. The wearable device and/or the patient monitoring and/or treatment system can further comprise a power source to provide power to the one or more ultrasonic transmitters, the one or more ultrasonic receivers, the one or more stimulating electrodes, the one or more recording electrodes, and the controller. The power source can comprise a wired power source and/or a wireless power source. The controller or another controller can be configured to control at least one of the one or more ultrasonic transmitters, the one or more ultrasonic receivers, the one or more stimulating electrodes, the one or more recording electrodes based on a trained machine-learning algorithm. The wearable device can further comprise one or more acoustic energy focusing elements that focuses the ultrasonic energy at the monitoring site and/or treatment site. The acoustic energy focusing elements, the one or more ultrasonic transmitters, the one or more ultrasonic receivers, the one or more stimulating electrodes, the one or more recording electrodes, or combinations thereof can be arranged as a single crystal, an annular ring, or a pad. The acoustic energy focusing elements, the one or more ultrasonic transmitters, the one or more ultrasonic receivers, the one or more stimulating electrodes, the one or more recording electrodes, or combinations thereof can be arranged in a 1D linear array of elements, a 1.5D array of elements, a 2D array of elements, a 2.5D array of elements, or a 3D array of elements. The acoustic energy focusing elements, the one or more ultrasonic transmitters, the one or more ultrasonic receivers, the one or more stimulating electrodes, the one or more recording electrodes, or combinations thereof can comprise flexible piezoelectric polymers, piezoelectric ceramics, and/or thin flexible composites. The attribute of the biological feature can be determined based on a difference in arrival times between the ultrasonic energy that is provided and the reflected ultrasonic energy or received ultrasonic energy. The wearable device can provide a signal representative of the attribute of the biological feature to an implantable device or an external control device that applies a treatment based on the attribute of the biological feature. The controller, another controller, transducer(s), and/or sensor(s) can further determine a heart rate based on the ultrasonic energy that is provided and the ultrasonic energy that is received or through other sensing/detecting modalities. The wearable device can further comprise a user display that displays the blood pressure and/or the heart rate. The wearable device can further comprise a communications interface for sending and/or receiving signals to/from a separate control device. The communications interface can receive signals from the separate control device to control when to take measurements of the biological feature. The wearable device can be incorporated into a wristwatch, a headset, an adhesive patch, a torniquet, a clothing, a bandage, an arm sleeve, an undergarment, a medical gown, and/or a textile. The wearable device can further comprise an inflatable member to allows for a release of moisture, oil, or ultrasound gel from the monitoring site and/or the treatment site. The patient monitoring and/or treatment system and/or the wearable device can further comprise one or more electromyography sensors, one or more accelerometry sensors, or both. The wearable device can further comprise a photoacoustic transceiver that provides light pulses to the monitoring site and/or the treatment site and receives ultrasound energy from the monitoring site and/or the treatment site. The wearable device can further comprise a photothermal transmitter and a thermal camera, wherein the photothermal transmitter provides light pulses to the monitoring site and/or the treatment site and the thermal camera detect thermal changes at the monitoring site and/or the treatment site. The wearable device is configured to perform deep-tissue temperature sensing.

In accordance with examples of the present disclosure, a method for patient monitoring and/or treatment is disclosed. The method comprises applying a wearable device configured to be wearable on an external portion of a patient, the wearable device configured to monitor and/or treat a biological feature of the patient by applying, using one or more ultrasonic transmitters, ultrasonic energy to a monitoring site and/or a treatment site of the patient; receiving, by one or more ultrasonic receivers, reflected ultrasonic energy from the monitoring and/or the treatment site; and controlling, by a controller, the one or more ultrasonic transmitter and the one or more ultrasonic receivers and determining an attribute of the biological feature based on the ultrasonic energy that is provided and the ultrasonic energy that is received.

Various additional features can be added to the method for patient monitoring and/or treatment including one or more of the following features. The biological feature can be a blood pressure, a tissue temperature, a tissue elasticity, or a volume of a target organ. The target organ can be a bladder, a liver, a brain, or another organ. The method for patient monitoring and/or treatment can further comprise providing, by one or more stimulating electrodes, therapeutic electrical stimulation to the monitoring site and/or the treatment site; recording, by one or more recording electrodes, neural activity at the monitoring site and/or the treatment site; and controlling, by the controller, the one or more stimulating electrodes and the one or more recording electrodes. The method for patient monitoring and/or treatment can further comprise providing power, by a power source, to the one or more ultrasonic transmitters, the one or more ultrasonic receivers, the one or more stimulating electrodes, the one or more recording electrodes, and the controller. The power source comprises a wired power source or a wireless power source. The method for patient monitoring and/or treatment can further comprise controlling, by the controller, at least one of the one or more ultrasonic transmitters, the one or more ultrasonic receivers, the one or more stimulating electrodes, the one or more recording electrodes based on a machine-learning algorithm. The method for patient monitoring and/or treatment can further comprise focusing, by one or more acoustic energy focusing elements, the ultrasonic energy at the monitoring site and/or treatment site. The acoustic energy focusing elements, the one or more ultrasonic transmitters, the one or more ultrasonic receivers, the one or more stimulating electrodes, the one or more recording electrodes, or combinations thereof can be arranged as a single crystal, an annular ring, or a pad. The acoustic energy focusing elements, the one or more ultrasonic transmitters, the one or more ultrasonic receivers, the one or more stimulating electrodes, the one or more recording electrodes, or combinations thereof can be arranged in a 1D linear array of elements, a 1.5D array of elements, a 2D array of elements, a 2.5D array of elements, or a 3D array of elements. The acoustic energy focusing elements, the one or more ultrasonic transmitters, the one or more ultrasonic receivers, the one or more stimulating electrodes, the one or more recording electrodes, or combinations thereof can comprise flexible piezoelectric polymers, piezoelectric ceramics, and/or thin flexible composites. The attribute of the biological feature can be determined based on a difference in arrival times between the ultrasonic energy that is provided and the reflected ultrasonic energy or received ultrasonic energy. The method for patient monitoring and/or treatment can further comprise providing a signal representative of the attribute of the biological feature to an implantable device or an external control device that applies a treatment based on the attribute of the biological feature. The method for patient monitoring and/or treatment can further comprise determining a heart rate based on the ultrasonic energy that is provided and the ultrasonic energy that is received. The method for patient monitoring and/or treatment can further comprise displaying the blood pressure and/or the heart rate on a user display of the wearable device. The method for patient monitoring and treatment can further comprise communicating, using a communications interface, signals to/from a separate control device. The method for patient monitoring and treatment can further comprise receiving signals from the separate control device to control when to take measurements of the biological feature. The wearable device can be incorporated into a wristwatch, a torniquet, a patch, a bandage, a headset, a clothing, an arm sleeve, an undergarment, a medical gown, or a textile. The method for patient monitoring and/or treatment can further comprise providing an inflating and/or a deflating signal to an inflatable member to allow for a release of moisture, oil, or ultrasound gel from the treatment site and/or the measurement site. The method for patient monitoring and/or treatment can further comprise receiving and/or providing signals to one or more electromyography sensors, one or more accelerometry sensors, or both.

BRIEF DESCRIPTION OF THE DRAWINGS

The accompanying drawings, which are incorporated in and constitute a part of this specification, illustrate certain embodiments, and together with the written description, serve to explain certain principles of the methods, devices, kits, systems, and related computer readable media disclosed herein. The description provided herein is better understood when read in conjunction with the accompanying drawings which are included by way of example and not by way of limitation. It will be understood that like reference numerals identify like components throughout the drawings, unless the context indicates otherwise. It will also be understood that some or all of the figures may be schematic representations for purposes of illustration and do not necessarily depict the actual relative sizes or locations of the elements shown.

DETAILED DESCRIPTION

As used in this specification and the appended claims, the singular forms “a,” “an,” and “the” include plural references unless the context clearly dictates otherwise. Thus, for example, a reference to “a method” includes one or more methods, and/or steps of the type described herein and/or which will become apparent to those persons skilled in the art upon reading this disclosure and so forth.

It is also to be understood that the terminology used herein is for the purpose of describing particular embodiments only and is not intended to be limiting. Further, unless defined otherwise, all technical and scientific terms used herein have the same meaning as commonly understood by one of ordinary skill in the art to which this disclosure pertains.

The present disclosure relates, in certain aspects, to systems, devices and methods for the monitoring of and treatment of injuries in humans. In some embodiments, the present disclosure relates, in certain aspects, to systems, devices and methods for the monitoring of and treatment of spinal cord injuries in humans or animals, although the system may be used for other types of injuries such as brain injuries, burn injuries, etc.

Embodiments disclosed herein provide a system and corresponding methods that can provide monitoring and stimulation of the spinal cord or area of an injury by utilizing an implantable device implantable near the injury. The implantable device may include a sensor to sense/image the injury and a first condition of the human related to the injury. The implantable device may also include a treatment device for treatment of the injury.

The system may also include a wearable device configured to be worn by the human. The wearable device may be configured to sense a second condition of the human related to the injury.

The system may further include a control device separate from the wearable device and the implantable device. The control device may receive signals from the wearable device and from the implantable device based on the sensed first and second conditions. In response to the signals, the control device may be configured to control the treatment device.

In some embodiments, the system is configured to monitor and treat spinal cord injuries (SCI), although other types of injuries could be monitored and treated. The implantable device may be configured to be implanted near the spinal cord injury or other type of injury to sense conditions of and treat the spinal cord injury or other injury.

Figure 1:
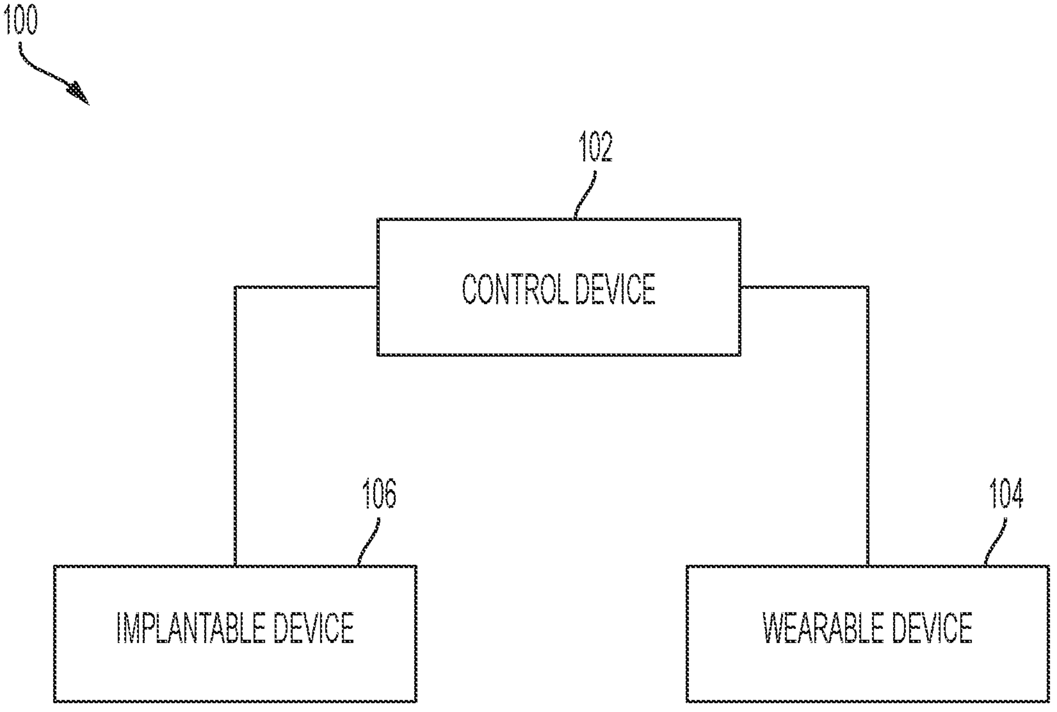
FIG. 1 schematically depicts a system according to an exemplary embodiment.

As shown in FIG. 1, a system 100 is configured for monitoring and treatment of injuries to a human body. The system may include a control device 102, a wearable device 104 and an implantable device 106. The control device 102 may be configured to control the system 100. The control device 102 is connected to the wearable device 104 and to an implantable device 106. The control device 102 may be connected to the wearable device 104 and to the implantable device 106 by a wired connection, such as by cables, but in certain preferred embodiments the control device 102 may be connected to the wearable device 104 and to the implantable device 106 by a wireless connection, such as Wi-Fi, Bluetooth, etc.

The wearable device 104 may be one wearable device or a plurality of wearable devices. The wearable device 104 is configured to be wearable on or in proximity to the human body. For example, the wearable device 104 may be attached by a strap or other means to a portion of the human body such as to an arm, a leg, a waist, a neck, etc. In alternative embodiments, the wearable device may be configured to be attached in proximity to a particular portion of the human body. For example, the wearable device 104 may be configured to be attached to clothes worn by a person. The wearable device 104 may also be integrated into or attached to another device worn by a person. For example, the wearable device 104 could be configured to attach to a watch, to a belt, to jewelry, etc.

The system 100 may additionally include a software application running on a device such as an Android tablet with an SCI-specific interface for both a physician and a patient that includes an API, allowing peripherals to use the application to change device settings to support closed-loop control of the therapy.

Figure 2:
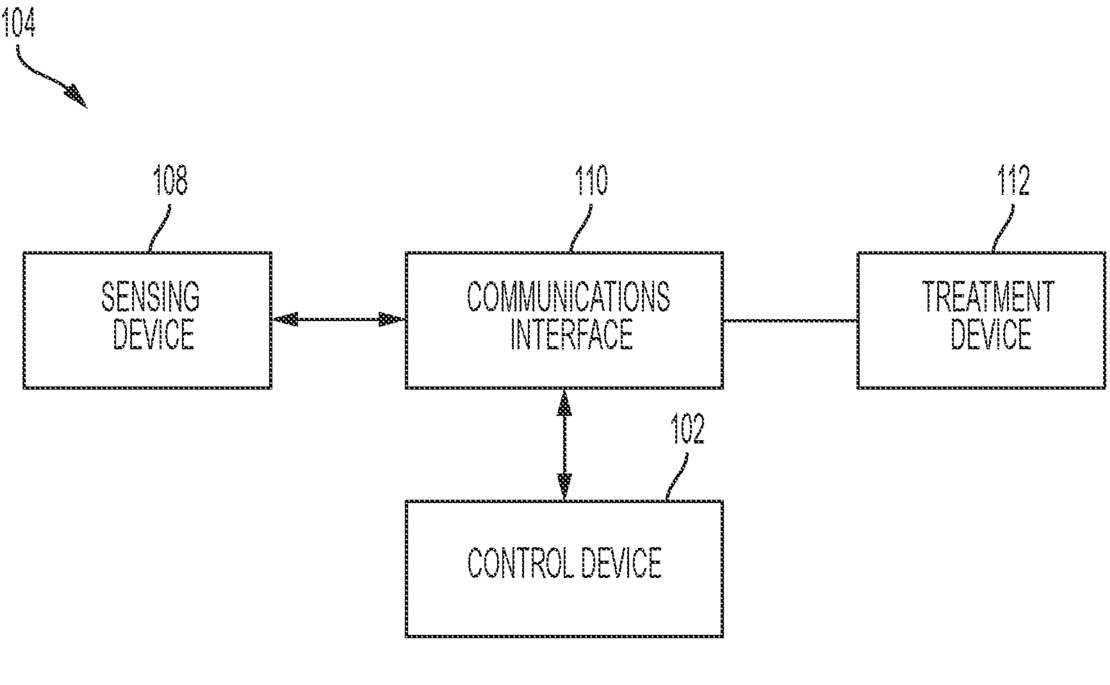
FIG. 2 schematically shows a wearable device according to one exemplary embodiment.

FIG. 2 illustrates further details of the wearable device 104. In certain embodiments, the wearable device may include a sensing device 108 configured to sense conditions of a human related to an injury. The sensing device 108 may be a sensor, imaging device or other type of sensing device configured to sense a condition of the human body related to an injury. For example, the sensing device 108, in some embodiments, may be configured to sense blood pressure, temperature, conditions related to a bladder such as pressure and volume, motion of human limbs such as an arm or a leg, etc.

The sensing device 108 may be any type of sensing device configured to sense a condition of the human body related to the injury. In some embodiments, the sensing device may be an imaging device, an ultrasound device, a temperature sensing device, an electromyography (EMG) sensor with accelerometers, a flow sensing device, a tissue perfusion sensing device, an elasticity measurement device, etc.

The wearable device 104 is some embodiments may include a treatment device 112, although other wearable devices 104 may omit the treatment device. The treatment device 112 may be configured to apply a treatment related to the injury. In some embodiments described herein the treatment device may be configured to apply an electrical stimulation or some other type of treatment, as further described herein.

The wearable device 104 may include a communications interface 110 for sending signals to the control device 102 and for receiving signals from the control device 102. The communications interface in some embodiments may be a wireless interface configured to send and receive signals to and from the control device 102. The signals may be indicative of the sensed conditions of the body related to the injury.

The control device 102 is configured to send and receive signals to the communications interface to control the sensing device 108 of the wearable device 104 and/or to control the treatment device 112. For example, the control device can be configured to cause the sensing device 108 to be activated to sense conditions and to cause the treatment device 112 to apply treatment to the human body.

Figure 3:
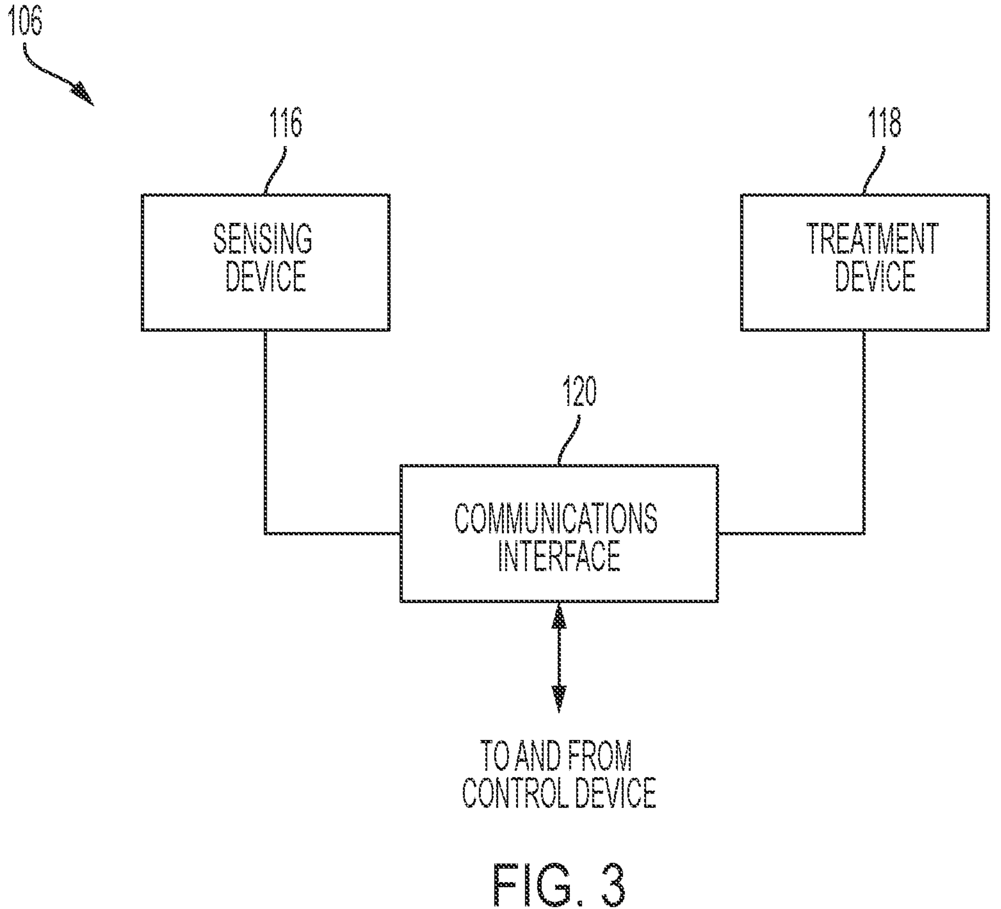
FIG. 3 schematically shows an implantable device according to one exemplary embodiment.

FIG. 3 illustrates the implantable device 106. The system 100 may include one implantable device or a plurality of implantable devices 106. The implantable device 106 is configured to be implanted within the human body. In some embodiments, the implantable device 106 may include a sensing device 116, a treatment device 118 and a communications interface 120.

The sensing device 112 may be configured to sense conditions of or related to an injury to a human. For example, the sensing device 112 may be an imaging device, a sensor or another type of sensing device. In some embodiments the sensing device may be an imaging device such as an ultrasound imaging device or other type of imaging device. In some embodiments, the sensing device 112 may be a sensor configured to sense conditions of a body related to an injury, such as a pressure sensor, a temperature sensor, a biomarker sensor, an EMG sensor, etc.

Figure 4:
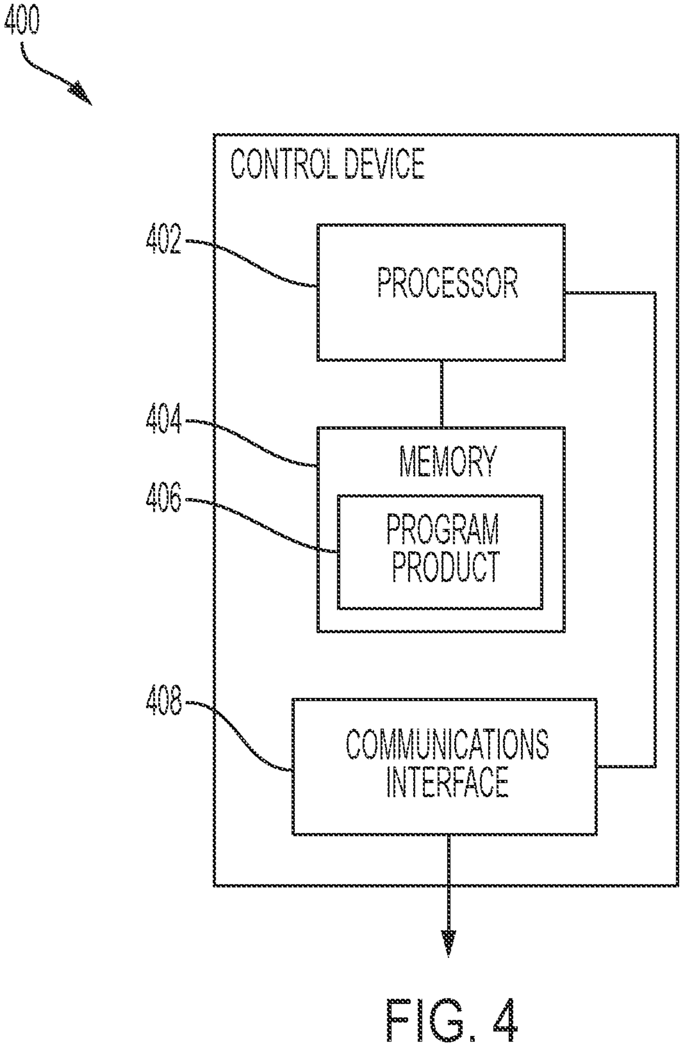
FIG. 4 schematically shows a control device according to one exemplary embodiment.

FIG. 4 illustrates the control device 400 which may be equivalent to the control device 102 of FIG. 1. The control device 400 may be a computerized device such as a desktop or laptop computer, a server computer, a smart phone, other mobile computing platforms, etc. The control device 400 includes a processor 402, a memory, storage device, or memory component 404, and a communications interface 408. The memory 404 optionally includes volatile and/or nonvolatile memory including, for example, RAM, ROM, and magnetic or optical disks, among others. The control device 400 may also include a display and a user interface (not shown). In certain aspects, the communications interface allows the control device 400 to send a receive signals to and from the implantable device 106 and the wearable device 104. The control device 400 also includes program product 406 stored in the memory 404.

Exemplary program product or machine readable medium 406 is optionally in the form of microcode, programs, cloud computing format, routines, and/or symbolic languages that provide one or more sets of ordered operations that control the functioning of the hardware and direct its operation. Program product 406, according to an exemplary aspect, also need not reside in its entirety in volatile memory, but can be selectively loaded, as necessary, according to various methodologies.

The term "computer-readable medium" or "machine-readable medium" refers to any medium that participates in providing instructions to a processor for execution. To illustrate, the term "computer-readable medium" or "machine-readable medium" encompasses distribution media, cloud computing formats, intermediate storage media, execution memory of a computer, and any other medium or device capable of storing program product 508 implementing the functionality or processes of various aspects of the present disclosure, for example, for reading by a computer. A "computer-readable medium" or "machine-readable medium" may take many forms, including but not limited to, non-volatile media, volatile media, and transmission media. Non-volatile media includes, for example, optical or magnetic disks. Volatile media includes dynamic memory, such as the main memory of a given system. Transmission media includes coaxial cables, copper wire and fiber optics, including the wires that comprise a bus. Transmission media can also take the form of acoustic or light waves, such as those generated during radio wave and infrared data communications, among others. Exemplary forms of computer-readable media include a floppy disk, a flexible disk, hard disk, magnetic tape, a flash drive, or any other magnetic medium, a CD-ROM, any other optical medium, punch cards, paper tape, any other physical medium with patterns of holes, a RAM, a PROM, and EPROM, a FLASH-EPROM, any other memory chip or cartridge, a carrier wave, or any other medium from which a computer can read.

In some aspects, program product 406 includes non-transitory computer-executable instructions which, when executed by electronic processor 402 perform at least: monitoring and treatment of injuries in a human by controlling the implantable device 106 and/or the wearable device 104. The systems and methods disclosed herein may include machine learning such that the systems can adapt by learning. For example, the system 100 can monitor how a human reacts to various treatments applied by the implantable device 106 and/or the wearable device 104 and learn how to better apply the treatments to various sensed conditions.

Figure 5:
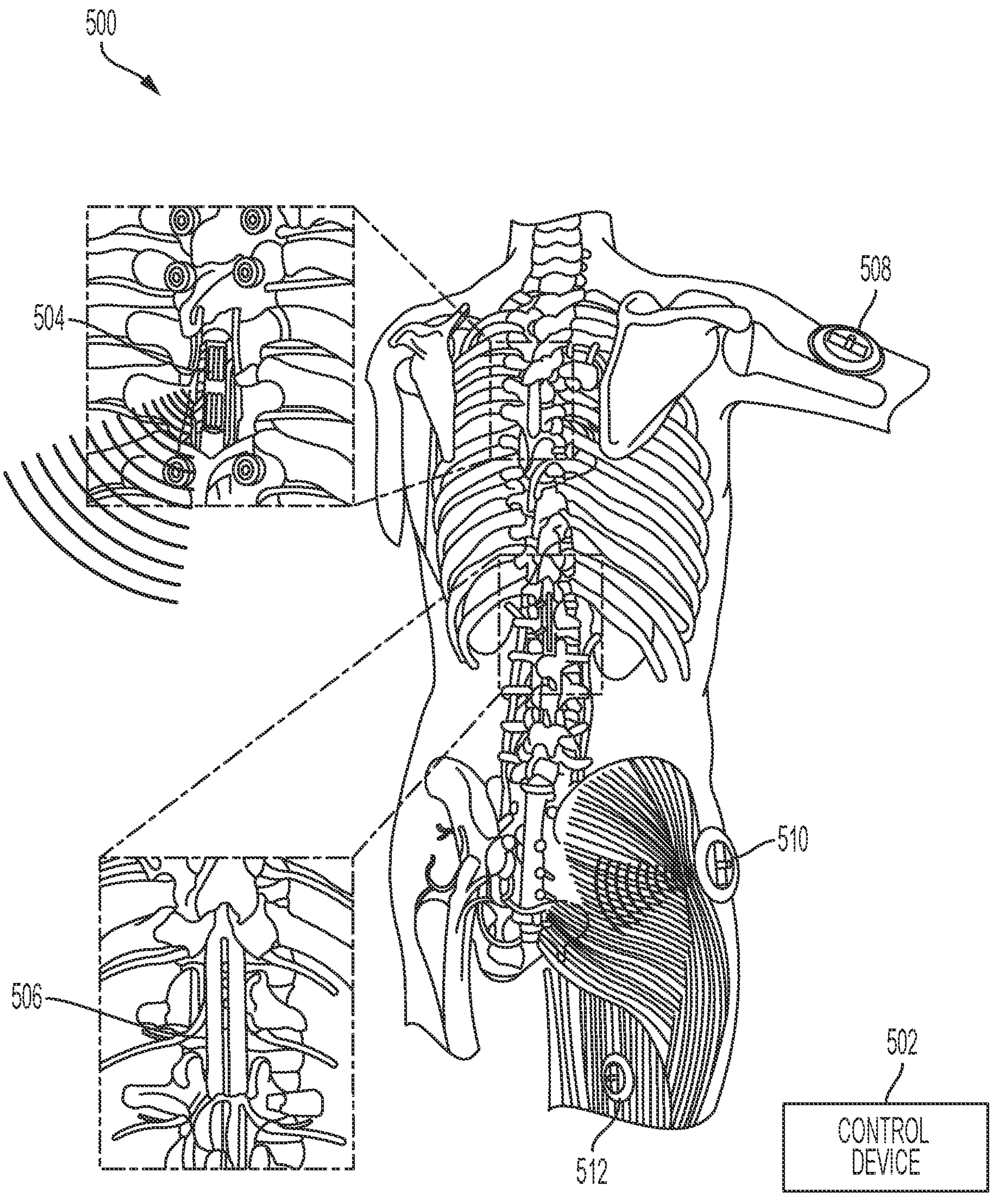
FIG. 5 is a schematic diagram of an exemplary system suitable for use with certain aspects disclosed herein.

FIG. 5 illustrates a system 500 according to a particular embodiment. The system 500 may be configured for monitoring and treatment of a spinal cord injury of a human, although the system 500 could be used for other types of injuries, such as a brain injury, etc. The system 500 includes a control device 502, a plurality of implantable devices 504 and 506, and a plurality of wearable devices 508, 510 and 512. One or more of the implantable devices 504 and 506 and the plurality of wearable devices 508, 510 and 512 could be omitted from the system 500. The control device 502 may be configured in a same manner as the control device 400.

The wearable device 508 may be a wearable device configured to sense a blood pressure, a tissue perfusion, an autoregulation of the spinal cord, etc., of a human wearing the wearable device. In FIG. 5, the wearable device is shown wearable over an arm of a human, although the wearable device 508 could be positioned in a different location, such as on a torso, a leg, etc. The wearable device 508 may include a sensing device to sense a blood pressure. The wearable device 508 may be configured to generate signals indicative of the sensed conditions, and to send the signals to the control device 102. The wearable device 508 may include means to affix to the body, such as a sticky surface, a strap, an inflatable member to allow for a release of moisture, moist, oil or gel, to the treatment site and/or the measurement site, etc.

The wearable device 510 may be a wearable device configured to sense a bladder volume and or bladder pressure of a human wearing the wearable device. In FIG. 5, the wearable device is shown. The wearable device 510 may include a sensing device to sense a bladder pressure and/or volume. The wearable device 510 may be configured to generate signals indicative of the sensed conditions, and to send the signals to the control device 102. The wearable device 510 may include means to affix to the body, such as a sticky surface, a strap, an inflatable member to allow for a release of moisture, moist, oil or gel, to the treatment site and/or the measurement site, etc.

The wearable device 512 may be an EMG wearable device configured to sense/detect motor functions of a human wearing the wearable device. In FIG. 5, the wearable device 512 is shown wearable in a leg area of a human, although the wearable device 512 could be positioned in a different location. The wearable device 512 may include a sensing device or devices to sense a motor functions. The wearable device 512 may be configured to generate signals indicative of the sensed conditions, and to send the signals to the control device 102. The wearable device 512 may include means to affix to the body, such as a sticky surface, a strap, an inflatable member to allow for a release of moisture, moist, oil or gel, to the treatment site and/or the measurement site, etc.

In some embodiments, a plurality of the wearable devices 512 may be utilized. For example, in some embodiments, a wearable device could be wearable on each arm and each leg, so that the system could monitor motor function of each arm and leg.

In some embodiments, the wearable device may include one or a plurality of accelerometers. In some embodiments, the accelerometers may be configured to generate signals indicative of a limb's motion in real time. The wearable device may be configured to send such signals to the control device 102.

The implantable device 504 may be a multi-function spinal cord implant (MUSIC). The multi-function spinal cord implant 504 may include one or more imaging or sensing devices and one or more treatment devices. In a preferred embodiment, the imaging devices may include an ultrasound imaging array or arrays to generate three- or four-dimensional images of the spinal cord at an injury location and an electrical array or arrays for electrical recording, although other types of imaging or sensing devices could be used. The treatment devices may include an electrical stimulation device or devices for applying electrical stimulation and a focused ultra-sound (FUS) device or devices for applying focused ultra-sound treatment, although other types of treatment devices may be used.

The multi-function spinal cord implant 504 may be a multimodal, conformal, wireless epidural implant device for use in patients with acute or chronic SCI. The multi-function spinal cord implant 504 may be configured to: a) produce three-dimensional, real-time, high-resolution imaging at the injury site to monitor and prevent secondary injury; b) evaluate and assess the reestablishment of autoregulation to optimize acute intervention; (c) measure biomarkers using aptamers; (d) enhance blood flow and potential neural regeneration as a result of acoustic neuromodulation/focused ultrasound (FUS) at the site of injury; (e) actuate release of encapsulated pharmacotherapeutic agents; (f) measure electrical conductivity above and below the site of injury; and (g) stimulate and record neurophysiological data with electrodes. In some embodiments, the multi-function spinal cord implant 504 may conform to the dorsal spinal cord while displacing a volume of only about 50 $mm^3$.

In some embodiments, the multi-function spinal cord implant 504 may be wirelessly powered from an external "relay station" attached outside the body at the implant site. This facilitates higher power levels without bulky battery implants. In some embodiments, the multi-function spinal cord implant 504 may communicate with the relay station via a custom ultra-wide-band networking protocol that may support 200 Mbps uplink and 100 Mbps downlink. The relay station may be an 802.11 device that communicates wirelessly with the control device 102.

In some embodiments, the multi-function spinal cord implant (MUSIC) 504 may be configured to interface with custom-designed encapsulating hydrogel scaffolds that can be stimulated with focused ultrasound (FUS) to deliver pharmacotherapeutic agents. FUS may also be used to enhance blood flow at the site of the injury. In some embodiments, the multi-function spinal cord implant 504 may be a biocompatible, permanently implantable wireless device.

The implantable device 506 may be a cerebrospinal fluid (CSF) management implant, also referred to as an acute CSF management implant (ACMI), 506, although other type of implantable devices could be used. In some embodiments, the ACMI 506 may be a smart spinal fluid drainage catheter. In some embodiments, the ACMI 506 may be configured to drain CSF while simultaneously using fiber optics technology to sense biomarkers such as intrathecal pressure, oxygenation, lactate, and temperature.

In some embodiments, ACMI 506 may include one or a plurality of sensors. The sensors may be configured to sense/detect temperature, pressure, and biomarkers. In some embodiments, the ACMI 506 may be configured to include optical sensors for measuring intrathecal pressure and temperature. In some embodiments, ACMI 506 may include sensors such as a fiber-optic, spectroscopy system that monitors spinal cord oxygenation by providing nearly continuous CSF concentration measurements of oxygenation indicators, such as lactate.

In some embodiments, ACMI 506 may include a drainage catheter to remove spinal fluid to adjust intraspinal pressure. In some embodiments, ACMI 506 measuring and managing CSF pressure throughout the acute phase of neurological injury.

Another implantable device may be utilized with the system 500, an epidural spinal stimulator (ESS) device. In some embodiments, the ESS device may be a biocompatible epidural implant. The ESS implantable device may be placed at the lumbosacral level (L1-S2), in the post-acute period of injury.

In some embodiments, the ESS device may be configured with electrodes configured to apply electrical stimulation of the spinal cord, particularly of the dorsal lumbosacral spinal cord. Dorsal epidural electrical stimulation does not induce movement by directly activating motor pools. Instead, it enables motor function by (1) stimulating medium- and large-diameter afferent fibers in lumbar and upper sacral posterior roots that transmit proprioceptive information from muscle spindle primary endings in the legs to the spinal cord and trans-synaptically engaging interneurons that integrate the proprioceptive inputs and central pattern generator networks. Epidural electrical stimulation modulates spinal circuits into a physiological state that allows for task-specific sensory input derived from movements to serve as a source of motor control.

In certain embodiments, motor outputs of the stimulation provided by the ESS device can be monitored and characterized by an accelerometer as well as by EMG potentials in target muscles. The EMG wearable device 512 may be used in conjunction with the ESS device in a manner that when the ESS device applies electrical stimulation, the EMG device monitors and generates signals indicative of the movement of the limbs of a human.

In some embodiments, properties of the signals generated by the EMG wearable device, such as latencies and peak-to-peak amplitudes, will be fed back to the epidural stimulation console to provide real-time information on locomotor output that are used to dynamically modulate and optimize stimulation parameters.

The ESS device may be configured to provide extremely fine temporal resolution (i.e., time resolution of 10 μs), increased independent rate options for programs providing therapy simultaneously, and independent amplitude control on each active electrode. The control device 102 may be configured with an ESS application programming interface (API), may be configured to wirelessly adjust the stimulation provided by the ESS device, at a rate of, for example, up to six times per second. In conjunction with intent information decoded from the individual's neural activity (the MUSIC device), posture and muscle-firing information (wearable EMG and accelerometer), bladder and CV parameters (wearable sensors), and machine learning algorithms for closed-loop neuromodulation, the ESS device is configured to be used to restore complex motor, bladder, and CV control.

In some embodiments, the ESS device is configured to be used along with the other elements of the system 100 to restore complex motor, bladder, and CV control to an individual with a SCI. For example, when electrical stimulation is provided by the ESS device, the control device can receive signals from the sensor devices to monitor motor, bladder, and CV control in response thereto.

In some embodiments, the ESS device can using a MICS band/Bluetooth relay, with USB or Bluetooth connection to the control device 102. MICS band communication will allow the control device to be several feet away from the patient while still providing therapy in a closed-loop manner through distance telemetry.

In some embodiments, the ESS device is configured to be implanted subcutaneously in the abdomen, flank, or upper buttock area, but could be implanted elsewhere. consists of a hermetic titanium enclosure housing stimulation and telemetry electronics with a battery. In some embodiments, the ESS device is configured to be used to stimulate the lumbar area of the spinal cord to provide SCI therapy.

In some embodiments, the system 100, 500 may be used to treat and monitor an individual with a SCI. For example, an individual with a SCI, such as a severe thoracic SCI, can have the ACMI device 506 implanted at subarachnoid space, and the MUSIC device 504 implanted epidurally at the site of the injury.

The ACMI device 506 is used for selectively draining CSF based on sensed feedback from its sensors. For example, the sensors the ACMI device may be configured to sense intrathecal pressure, oxygenation, lactate, and temperature, and feed signals indicative of the sensed conditions to the control device 102. The control device can control the ACMI device 506 to then selectively draining CSF based on analyzing the signals.

The MUSIC device 504 utilizes its ultrasound and/or electrical imaging sensors to generate three-dimensional, real-time, high-resolution imaging at the injury site to monitor and prevent secondary injury, and to selectively provide acoustic neuromodulation and/or focused ultrasound (FUS) at the site of injury. The MUSIC device 504 may be configured to generate signals/images based on conditions sensed by its sensors, and to send those signals to the control device 102. The control device 102 may be configured to selectively provide acoustic neuromodulation and/or focused ultrasound based on analyzing the received signals.

In a post-acute period, the ESS device may be implanted, and the wearable devices 104 may be worn and utilized with the system 100, 500. The ESS device may be configured to selectively apply electrical stimulation of the dorsal lumbosacral spinal cord based on sensed conditions from any of the wearable devices 104 or the implantable devices 106.

The system 100, 500 includes software programs (algorithms) as program product 406 that include a machine-learning modelling framework. All sensed data may be loaded to a persistent datastore. The data in the datastore is used with a real-time implementation of a multimodal time-series classification network built on efficient implementations of deep convolutional neural networks for processing multi-scale spatiotemporal representations. The networks are trained to predict optimal interventions (e.g., stimulation with electrodes, ultrasound, and drug delivery)

based on simultaneous analysis of the MUSIC implant's electrode array, ultrasound measurements, and ACMI biomarker inputs, for example. Regression models based on deep features extracted from ultrasound using convolutional neural networks, can be used to estimate bladder state and blood pressure. As the amount of chronic data in the datastore increases and more functionality is demanded from the system, the algorithms are trained and deployed to predict improved stimulation patterns from multimodal inputs.

The present disclosure also provides various systems and computer program products or machine readable media. In some aspects, for example, the methods described herein are optionally performed or facilitated at least in part using systems, distributed computing hardware and applications (e.g., cloud computing services), electronic communication networks, communication interfaces, computer program products, machine readable media, electronic storage media, software (e.g., machine-executable code or logic instructions) and/or the like.

As understood by those of ordinary skill in the art, memory 404 of the control device 400 optionally includes volatile and/or nonvolatile memory including, for example, RAM, ROM, and magnetic or optical disks, among others. It is also understood by those of ordinary skill in the art that although illustrated as a control device, the illustrated configuration of control device 400 is given only by way of example and that other types of servers or computers configured according to various other methodologies or architectures can also be used. As also understood by those of ordinary skill in the art, the control device 400, for example, can be a laptop, desktop, tablet, personal digital assistant (PDA), cell phone, server, or other types of computers.

As further understood by those of ordinary skill in the art, exemplary program product or machine readable medium 406 is optionally in the form of microcode, programs, cloud computing format, routines, and/or symbolic languages that provide one or more sets of ordered operations that control the functioning of the hardware and direct its operation. Program product 406, according to an exemplary aspect, also need not reside in its entirety in volatile memory, but can be selectively loaded, as necessary, according to various methodologies as known and understood by those of ordinary skill in the art.

As further understood by those of ordinary skill in the art, the term "computer-readable medium" or "machine-readable medium" refers to any medium that participates in providing instructions to a processor for execution. To illustrate, the term "computer-readable medium" or "machine-readable medium" encompasses distribution media, cloud computing formats, intermediate storage media, execution memory of a computer, and any other medium or device capable of storing program product 508 implementing the functionality or processes of various aspects of the present disclosure, for example, for reading by a computer. A "computer-readable medium" or "machine-readable medium" may take many forms, including but not limited to, non-volatile media, volatile media, and transmission media. Non-volatile media includes, for example, optical or magnetic disks. Volatile media includes dynamic memory, such as the main memory of a given system. Transmission media includes coaxial cables, copper wire and fiber optics, including the wires that comprise a bus. Transmission media can also take the form of acoustic or light waves, such as those generated during radio wave and infrared data communications, among others. Exemplary forms of computer-readable media include a floppy disk, a flexible disk, hard disk, magnetic tape, a flash drive, or any other magnetic medium, a CD-ROM, any other optical medium, punch cards, paper tape, any other physical medium with patterns of holes, a RAM, a PROM, and EPROM, a FLASH-EPROM, any other memory chip or cartridge, a carrier wave, or any other medium from which a computer can read.

Program product 406 is optionally copied from the computer-readable medium to a hard disk or a similar intermediate storage medium. When program product 406, or portions thereof, are to be run, it is optionally loaded from their distribution medium, their intermediate storage medium, or the like into the execution memory of one or more computers, configuring the computer(s) to act in accordance with the functionality or method of various aspects. All such operations are well known to those of ordinary skill in the art of, for example, computer systems.

To further illustrate, in certain aspects, this application provides systems that include one or more processors, and one or more memory components in communication with the processor. The memory component typically includes one or more instructions that, when executed, cause the processor to provide information that causes at least one result, data, and/or the like to be displayed or otherwise indicated (e.g., via a result indicator of control device 400) and/or receive information from other system components and/or from a system user (e.g., via communication interface 408 or the like).

In some aspects, program product 406 includes non-transitory computer-executable instructions which, when executed by electronic processor 402 perform at least execution of algorithms contained in the computer program product 406 configured to perform the functionality described herein.

Figure 6:
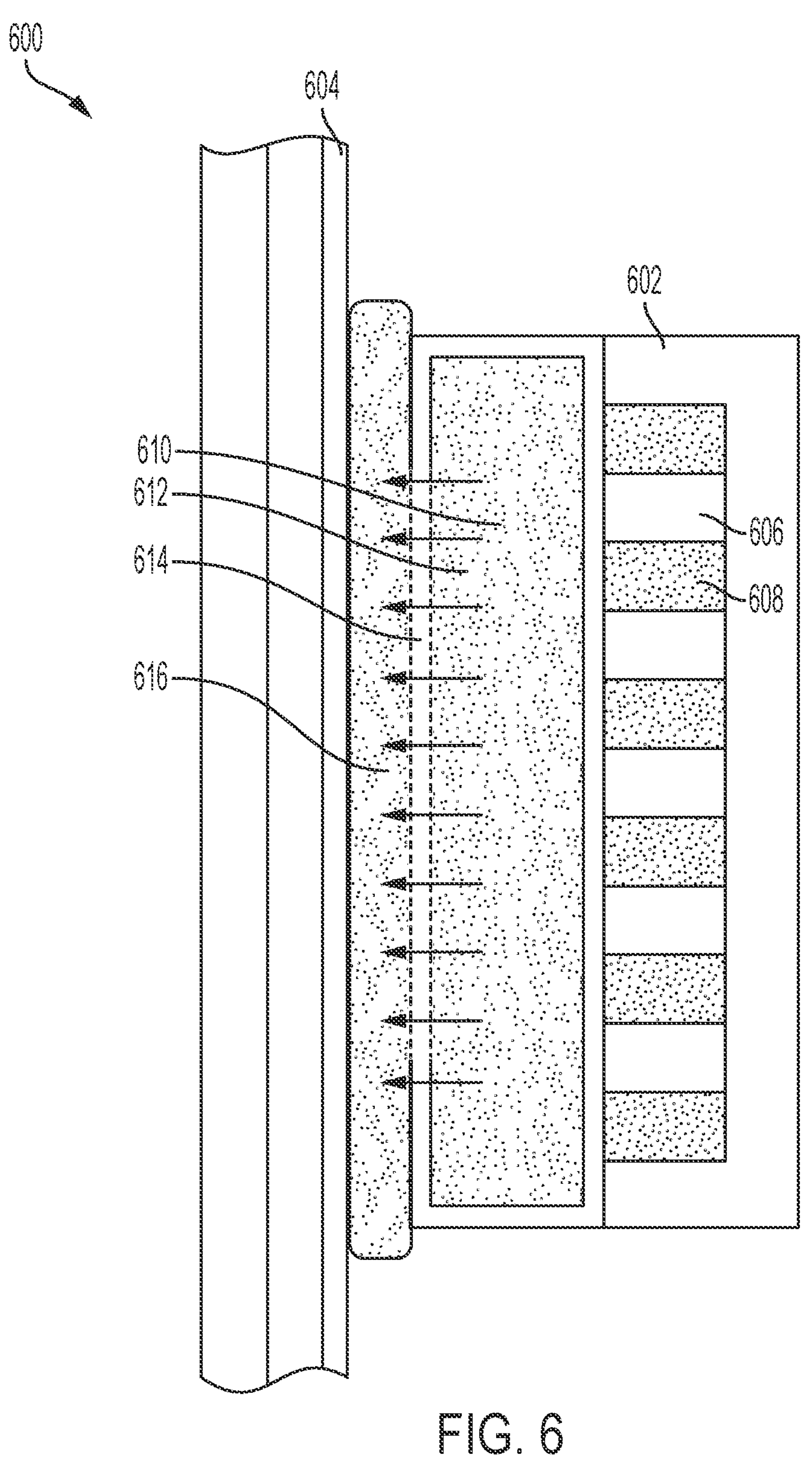
FIG. 6. shows a side view of wearable device according to examples of the present disclosure.

The wearable device 104 of FIG. 1 and/or the plurality of wearable devices 508, 510 and 512 of FIG. 5 are now discussed in further detail below. FIG. 6 shows a side view of wearable device 600 according to examples of the present disclosure. Wearable device 600 can be used as the wearable device 104 of FIG. 1 and/or the plurality of wearable devices 508, 510 and 512 of FIG. 5. Wearable device 600 can be configured to be wearable on an external portion of the patient. Wearable device 600 can be configured to monitor and/or treat a biological feature of the patient. For example, the biological feature can be a blood pressure, a volume of a target organ, an area of the skin, or another biological feature. For example, the target organ is a bladder, a liver, a brain, the skin, or another organ. In some examples, the treatment can be for a chronic pain, a skin irritation (itch), or other disease or discomfort. In some examples, the wearable device can be in the form of a patch that includes a receiver that receives signals from organs, such as the liver or spinal cord, where the pulsatility of the micro-vasculature can be detected on their own without the need for transmission of ultrasound energy. Wearable device 600 can be configured as a blood pressure monitor, a heart rate monitor, a temperature monitor, an organ volume monitor, an electromyography monitor, an accelerometry tracking monitor, or any combination thereof of the monitors. In some examples, wearable device 600 can be configured to perform remote deep-tissue temperature sensing using ultrasound thermometry. The temperature can be determined based on how changes in temperature affect the speed of sound, and hence the propagation and time-of-flight of the ultrasonic waves. Wearable device 600 can be incorporated into a wristwatch, a torniquet, a clothing, a textile, a patch, a bandage, a headset, an arm sleeve, an undergarment, a medical gown, or another device or appliance. For example, textile, the patch, the bandage, the arm sleeve, the torniquet, and/or the clothing that incorporates or uses wearable device 600 can comprises or at least partially composed, or formed from polyvinylidene fluoride (PVDF), which is a high purity engineering thermoplastic that has excellent chemical resistance, abrasion resistance, flame resistance, and UV stability.

In some examples, wearable device 600 can provide for one or more of the following features: imaging flow sensing, continuous monitoring of tissue perfusion, early detection of stroke onset when used on the head or neck, elastography, whereby the elasticity/stiffness of the tissue is being mapped, the ability to visualize slow flow in small microvasculature. We can claim the capability of the device to conduct and provide data comparable to Canon's SMI (Superb Microvascular Imaging) or Philip's MFI (Microflow imaging) modalities, drug delivery, remote ablation of tumors and cysts, neuromodulation/ultrasound stimulation, for treatment of chronic pain and itching.

In some examples, wearable device 600 can provide for diagnostic ultrasound (for imaging, monitoring flow, etc), therapeutic ultrasound (for neuromodulation, or treatments of itch, pain, cysts, etc), diagnostic electrodes (to record neural activity), and therapeutic electrodes (for electrical stimulation).

Wearable device 600 can be configured to include one or more transducers 602 that are touching or are in close contact with skin 604 of the patient. One or more transducers 502 can include one or more transmitting modules (Send 606) and/or one or more receiving modules (Receive 608). The one or more transmitting modules (Send 606) can include one or more ultrasonic transmitters that provide ultrasonic energy to a monitoring site and/or a treatment site of the patient. Additionally or alternatively, the one or more transmitting modules (Send 606) can include one or more stimulating electrodes that provide therapeutic electrical stimulation to the monitoring site and/or the treatment site. The one or more receiving modules (Receive 608) can include one or more ultrasonic receivers that receive reflected ultrasonic energy from the monitoring site and/or the treatment site. Additionally or alternatively, the one or more receiving modules (Receive 608) can include one or more recording electrodes that provide recording of neural activity at the monitoring site and/or the treatment site. Additionally or alternatively, one or more transducers 502 can include one or more electromyography sensors, one or more accelerometry sensors, or both.

Wearable device 600 can further optionally comprises an inflatable member, such as a bladder 610, to allow for a release of moisture, moist, oil or gel from the device on the skin or the monitoring site and/or the treatment site. In some examples, the inflatable member can be in the form of a water bladder or balloon that has small pores allowing for small and slow release of moisture, so that it allows for best contact with the skin. This allows for coupling of the ultrasound or ultrasound gel with the skin. In some examples, the inflatable member can be a tiny, thin and flexible (and porous) water balloon foil that allows for slow release of small amount of moisture to facilitate ultrasound contact with the skin or on the non-hairy portions of the skull.

Wearable device 600 can further optionally comprises an acoustic membrane 612. This acoustic membrane can act as an acoustic matching layer to increase acoustic efficiency of the device, as well as to reduce energy loss at the interface. In some embodiments, this membrane can be biocompatible, biodegradable or bioresorbable.

Wearable device 600 can further optionally comprise a fenestrated membrane 614. This fenestrated membrane can hold fluid or gas, such as moist, moisture, oil, ultrasound gel or other materials that can facilitate better contact with the skin. In some embodiments, this membrane can be biocompatible, biodegradable or bioresorbable.

Wearable device 600 can further optionally one or more apertures 616 that allows the medium to leak onto the skin. These apertures can be in form of pores at the interface of items 614 and the skin. In some embodiments, this membrane can be biocompatible, biodegradable or bioresorbable.

In some examples, wearable device 600 can be held in place using a negative pressure (i.e. instead of a push on the skin or target tissue). Wearable device 600 can be placed on a sticky gel that due its stickiness, allows proper contact between the tissue/skin and wearable device 600. In some examples, the gel is made out of both biocompatible and sonolucent materials. The materials can be chosen in a manner that its acoustic properties (e.g. speed of sound and attenuation) allows for passage of ultrasonic waves without production of non-desirable echoes. In some examples, the gel can be a hydrogel, e.g. a photocrosslinkable gel (i.e. where wearable device 600 is positioned on the patient and a light, such as UV light, is used to make sure the gel gets solidified and sticky enough for proper contact with the body). In other examples, the gel can be a shear-thinning material (STM), such as materials that respond to pressure and make a solid paste become more liquified and easy to move. In other examples, the gel can be shear-thinning biomaterials (STB) that are used for proper contact with the body, as well as to facilitate better ultrasound energy transfer from wearable device 600 to the body. The STM/STB can be placed on the skin and when wearable device 600 is pressed on it, it liquifies just enough to accommodate wearable device 600 and establish appropriate contact with the body. After which point, the gel solidifies and hence keeps wearable device 600 on its intended placement.

Wearable device 600 and/or control device 102 can comprise a controller that controls the one or more ultrasonic transmitter and the one or more ultrasonic receivers and determines an attribute of the biological feature based on the ultrasonic energy that is provided and the ultrasonic energy that is received. The controller can further control the one or more stimulating electrodes and the one or more recording electrodes. The controller can be configured to control at least one of the one or more ultrasonic transmitters, the one or more ultrasonic receivers, the one or more stimulating electrodes, the one or more recording electrodes based on a trained machine-learning algorithm. In some examples, the controller can determine the attribute of the biological feature based on a difference in arrival times between the ultrasonic energy that is provided and the reflected ultrasonic energy or received ultrasonic energy. In some examples the controller can provide a signal representative of the attribute of the biological feature to the implantable device 106 or an external control device, such as the control device 102, that applies a treatment based on the attribute of the biological feature. In some examples, the controller can further determine a blood pressure based on the ultrasonic energy that is provided and the ultrasonic energy that is received.

Wearable device 600 can further comprise a user display that displays the blood pressure, the heart rate, another biological feature, or combinations thereof. Wearable device 600 can further comprise a communications interface, such as communications interface 110, for sending and receiving signals to/from a separate control device, such as control device 102, sensing device 108, or treatment device 112. The communications interface can receive signals from the separate control device, such as control device 102, sensing device 108, or treatment device 112, to control when to take measurements of the biological feature.

Wearable device 600 and/or control device 102 can comprise a power source to provide power to the one or more ultrasonic transmitters, the one or more ultrasonic receivers, the one or more stimulating electrodes, the one or more recording electrodes, and the controller. The power source comprises a wired power source and/or a wireless power source. In some examples, the power source can include solar panels. In some examples, wearable device 600 can be powered through a force applied on a patient's shoes. e.g. a pad within the shoes. In some examples, wearable device 600 can be powered though Bluetooth with portable phones and tablets, e.g. when the patient opens the app to monitor their heart rate, blood pressure or bladder volume, the app asks for permission to connect wirelessly with wearable device 600 to power them remotely.

Wearable device 600 can further optionally comprise one or more acoustic energy focusing elements that focuses the ultrasonic energy at the monitoring site and/or the treatment site. In some examples, the acoustic energy focusing elements, the one or more ultrasonic transmitters, the one or more ultrasonic receivers, the one or more stimulating electrodes, the one or more recording electrodes, or combinations thereof are arranged as a single crystal, an annular ring, or a pad. In some examples, the acoustic energy focusing elements, the one or more ultrasonic transmitters, the one or more ultrasonic receivers, the one or more stimulating electrodes, the one or more recording electrodes, or combinations thereof are arranged in a 1D linear array of elements, a 1.5D array of elements, a 2D array of elements, a 2.5D array of elements, or a 3D array of elements. In some examples, the acoustic energy focusing elements, the one or more ultrasonic transmitters, the one or more ultrasonic receivers, the one or more stimulating electrodes, the one or more recording electrodes, or combinations thereof comprise flexible piezoelectric polymers, piezoelectric ceramics, or thin flexible composites.

In some examples when wearable device 600 functions as a blood pressure monitor, wearable device 600 can be an MR-compatible (or MR-safe), 5-MHz 64-element, 1D (linear) phased array. In another example, the wearable device 600 can include a 1024 by 1024 two-dimensional array. For example, the frequency range for therapeutic ultrasound can be between about 0.5 MHz to about 5 MHz and the frequency range for imaging/diagnostic ultrasound can be between about 1 MHz to about 35 MHz. Wearable device 600 or control device 102 can perform functions of optimizing scripting, beamforming, and reconstruction optimization. Blood pressure measurements can be be derived by visualization of the blood flow and blood vessel wall motion. The transducer array (one or more transducers 602) can be constructed using a piezoceramic composite structure on a (2 pitch with 10 mm elevation width.

The transducer array (one or more transducers 602) can be constructed using non-ferrous and non-residual magnetism materials, as well as layers that are matched between surfaces to avoid artefacts. The front layer can provide dielectric protection between the stack's ground electrode and the patient. The transducer array (one or more transducers 602) can be configured as an ultrasound transceiver ASIC (Application Specific Integrated Circuit) chip, to support a phased array configuration, e.g. with a center frequency of 15- or 20-MHz. The ASIC can be mounted on a printed circuit board (PCB) that can also provide wireless capabilities, power management, and streaming of ultrasound image slices over Bluetooth low energy radio.

In some examples when wearable device 600 functions as an organ monitor, such as a bladder fill volume imaging and pressure sensor, wearable device 600 can be a MR-compatible (or MR-safe), 2D array that provides for imaging of a volume of the target organ, such as a bladder, in a patient. The transducer array (one or more transducers 602) can be optimized for scripting, beamforming, and reconstruction optimization. The transducer array (one or more transducers 602) can be constructed using a 16×16 element matrix (256 elements total). The 2D array can be asymmetric in construction because the angular width of the bladder, as viewed from the lower abdomen, is large in a transverse plane. The 2D arrays can specify a center frequency and azimuth and elevation pitch, and may be on the order of 2 to 4 MHz, □□pitch along the transverse (azimuthal) direction, and 2 to 2.5 □□along the midline (elevation). An elevation lens can be used to tilt the beam downward in the midplane, improving performance and eliminating the need for more elements. One matching layer can acoustically match the transducer array to soft tissue using □4 thickness.

In some examples, wearable device 600 can function as an electromyography and accelerometry tracking sensor, such as by using the transducer array (one or more transducers 602), which can interface with a spinal interface to produce motor movements. In this example, wearable device 600 can be integrated with a microelectromechanical systems (MEMS) accelerometer that can provide separate voltage signals conveying each limb's motion in real-time. A machine-learning technique can be used to analyze the signal patterns, estimate force, and correlate with movements.

In some examples, wearable device 600 can further comprise a photoacoustic transceiver that provides light pulses to the monitoring site and/or the treatment site and receives ultrasound energy from the monitoring site and/or the treatment site, such as by using the transducer array (one or more transducers 602). In some examples, wearable device 600 can further comprise a photothermal transmitter and a thermal camera, such as by the transducer array (one or more transducers 602), wherein the photothermal transmitter provides light pulses to the monitoring site and/or the treatment site and the thermal camera detects thermal changes at the monitoring site and/or the treatment site.

Figure 7:
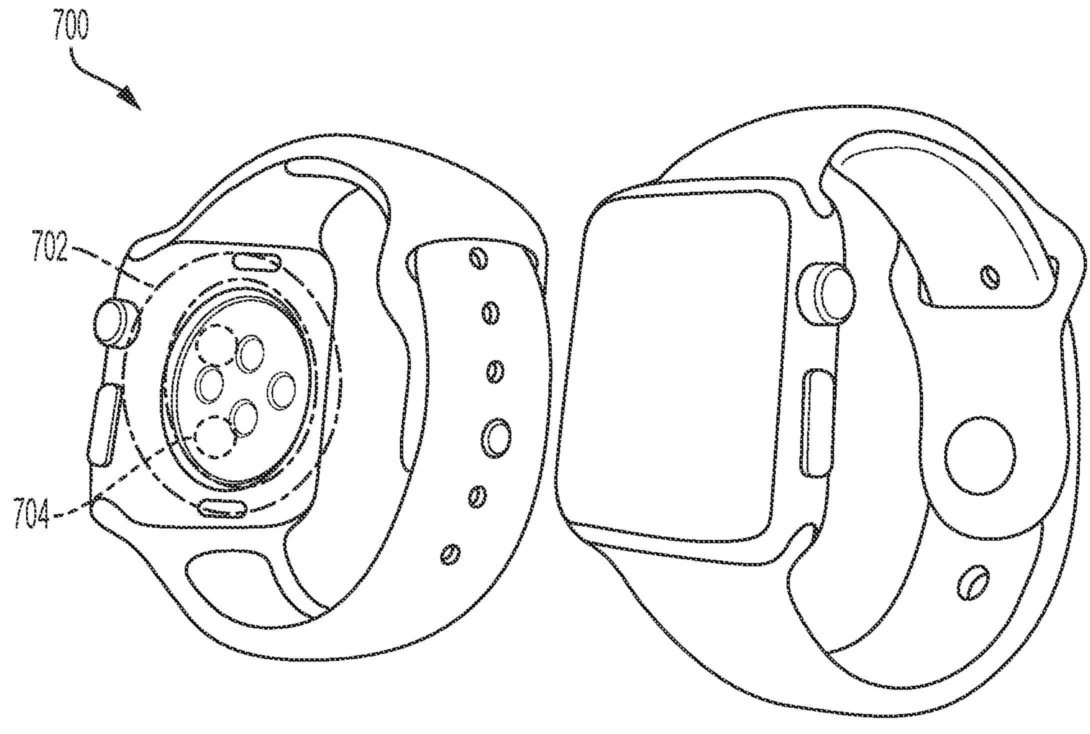
FIG. 7 shows an example of a wearable device that is incorporated into a wristwatch according to examples of the present disclosure.

FIG. 7 shows an example of wearable device 600 that is incorporated into wristwatch 700 according to examples of the present disclosure. On the back of the wristwatch 700 that is in contact with the skin, one or more transducers 704, such as one or more transducers 602 of FIG. 6, and moisture-release layer 702. The front of the wristwatch 700 can include a user interface, such as the user interface discussed with FIG. 6.

Figures 8, 9, 10:
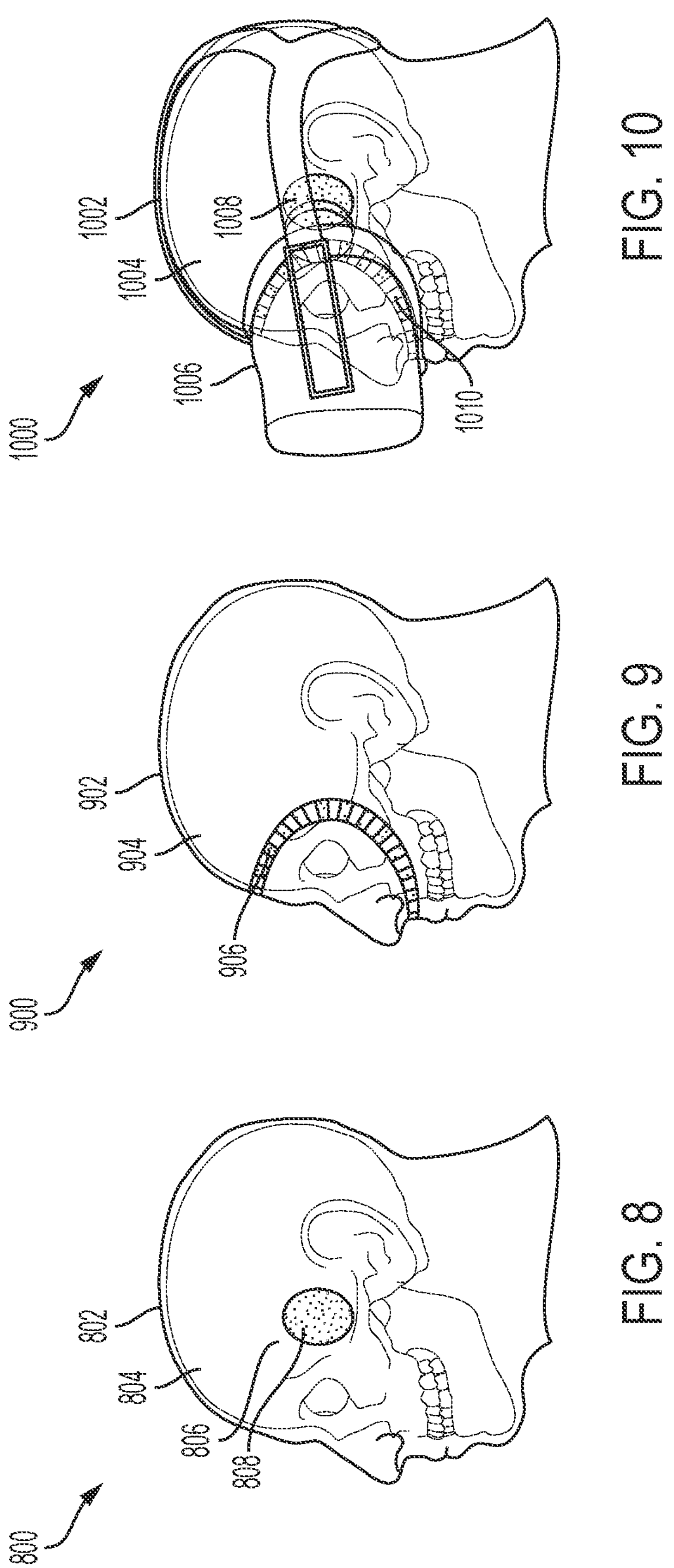
FIG. 8 shows a first example of a wearable device attached to a head of a patient according to examples of the present disclosure.
FIG. 9 shows a second example of a wearable device attached to a head of a patient according to examples of the present disclosure.
FIG. 10 shows a third example of a wearable device attached to a head of a patient according to examples of the present disclosure.

FIG. 8 shows a first example of wearable device 800 attached to a head of a patient according to examples of the present disclosure. In the example shown, wearable device 800 includes one or more transducers 808, such as one or more transducers 602 of FIG. 6, connected to temple 806 of skull 804 of head 802 of the patient. FIG. 9 shows a second example of wearable device 900 attached to a head of a patient according to examples of the present disclosure. In the example shown, wearable device 900 includes one or more transducers 906, such as one or more transducers 602 of FIG. 6, connected to the front and side of skull 904 of head 902 of the patient. FIG. 10 shows a third example of wearable device 1000 attached to a head of a patient according to examples of the present disclosure. In the example shown, wearable device 1000 includes one or more temple transducers 1008 and one or more periocular transducers 1010, such as one or more transducers 602 of FIG. 6, connected to headset 1006, which is connected to skull 1004 of head 1002 of the patient.

Figure 12:
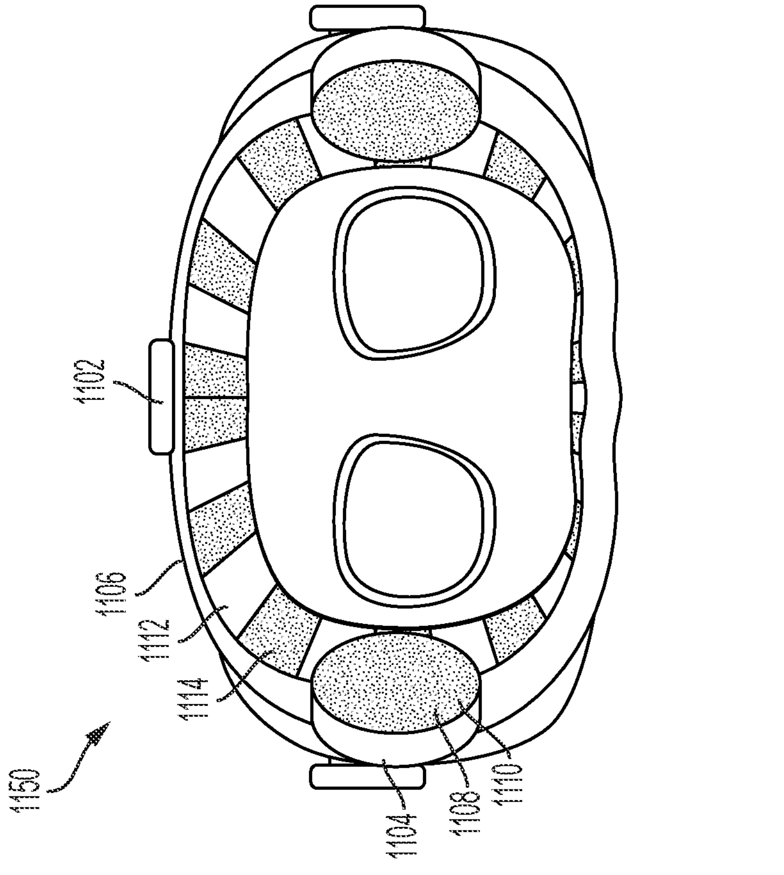
FIG. 12 shows a front view of FIG. 11.
Figure 11:
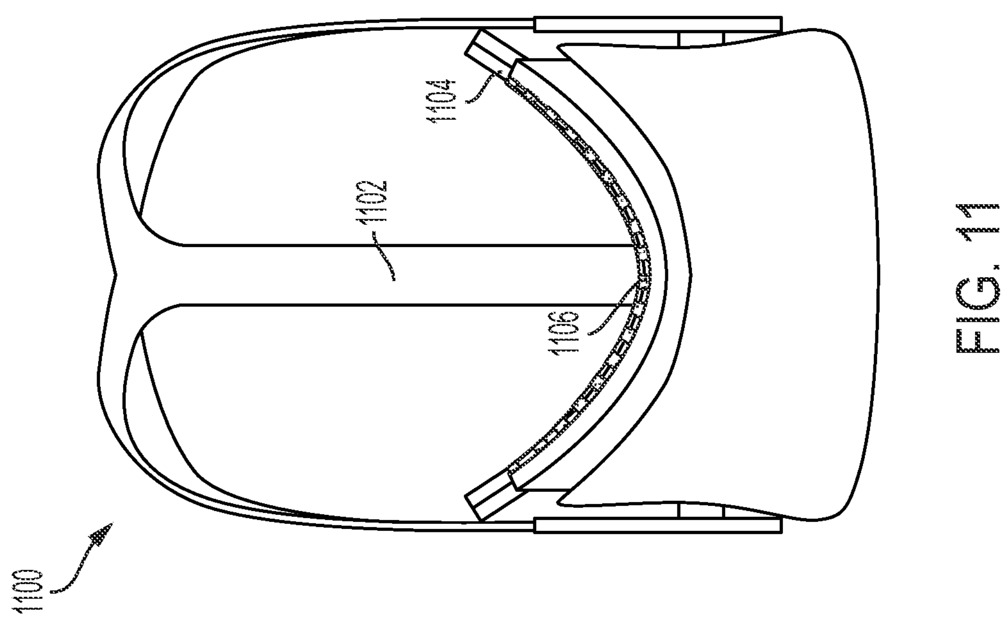
FIG. 11 shows a top view of another example of a wearable device that is incorporated into headset 1100 according to examples of the present disclosure.
Figure 13:
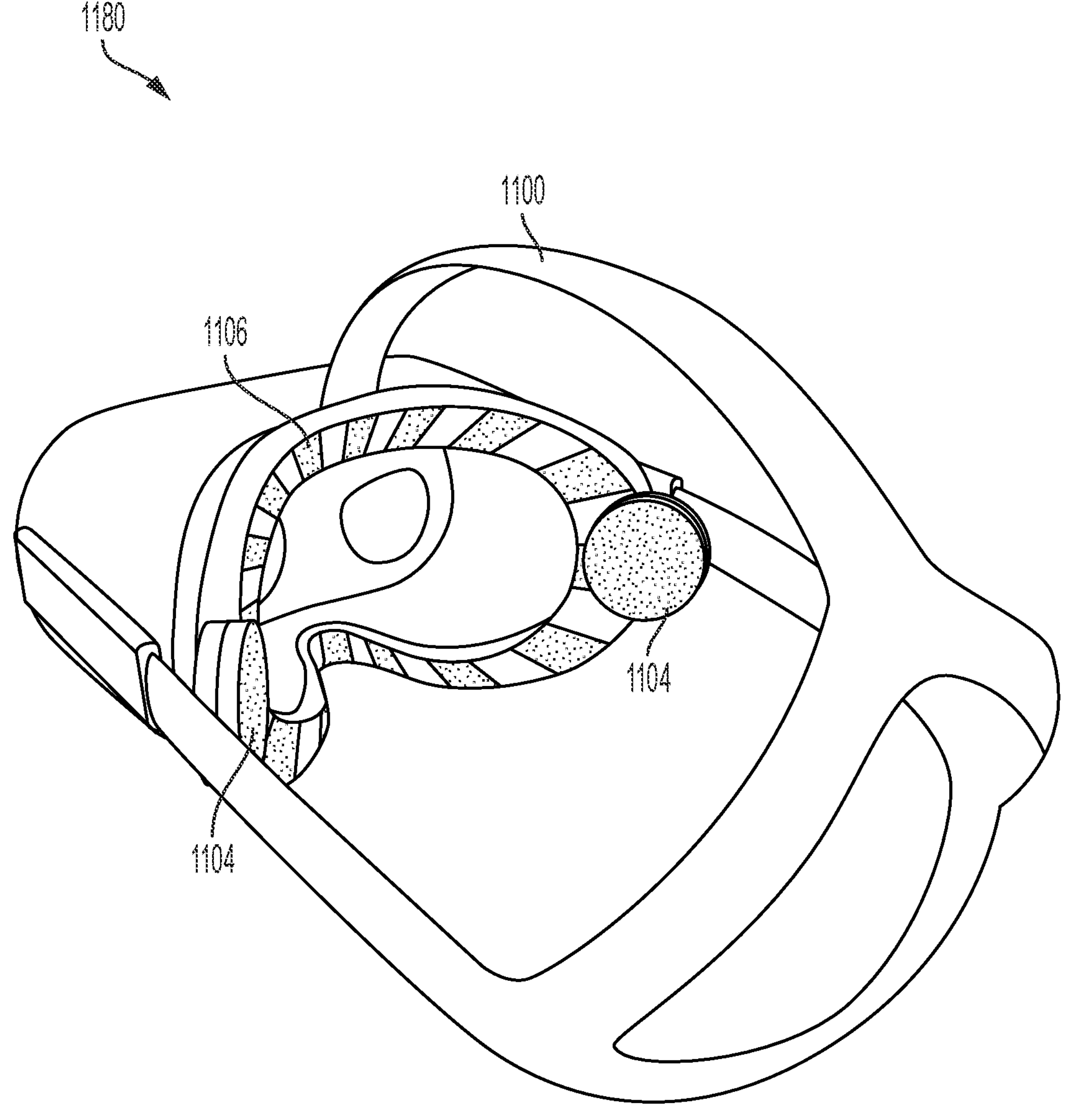
FIG. 13 shows a perspective view of FIG. 11.

FIG. 11 shows a top view 1100 of another example of wearable device 600 that is incorporated into headset 1100 according to examples of the present disclosure. FIG. 12 shows a front view 1150 of FIG. 11. FIG. 13 shows a perspective view 1180 of FIG. 11. As shown in FIG. 11, headset 1102 comprises one or more temple transducers 1104 and one or more periocular transducers 1106, such as one or more transducers 602 of FIG. 6. As shown in FIG. 12, headset 1102 comprises one or more temple transducers 1104, which comprise one or more transmitting modules (Send 1108) and/or one or more receiving modules (Receive 1110), as described above in FIG. 6, and one or more periocular transducers 1106, which comprise one or more transmitting modules (Send 1112) and/or one or more receiving modules (Receive 1114), as described above in FIG. 6.

Figure 14:
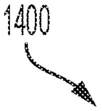
FIG. 14 shows a method for patient monitoring and/or treatment according to examples of the present disclosure.
Figure 14:
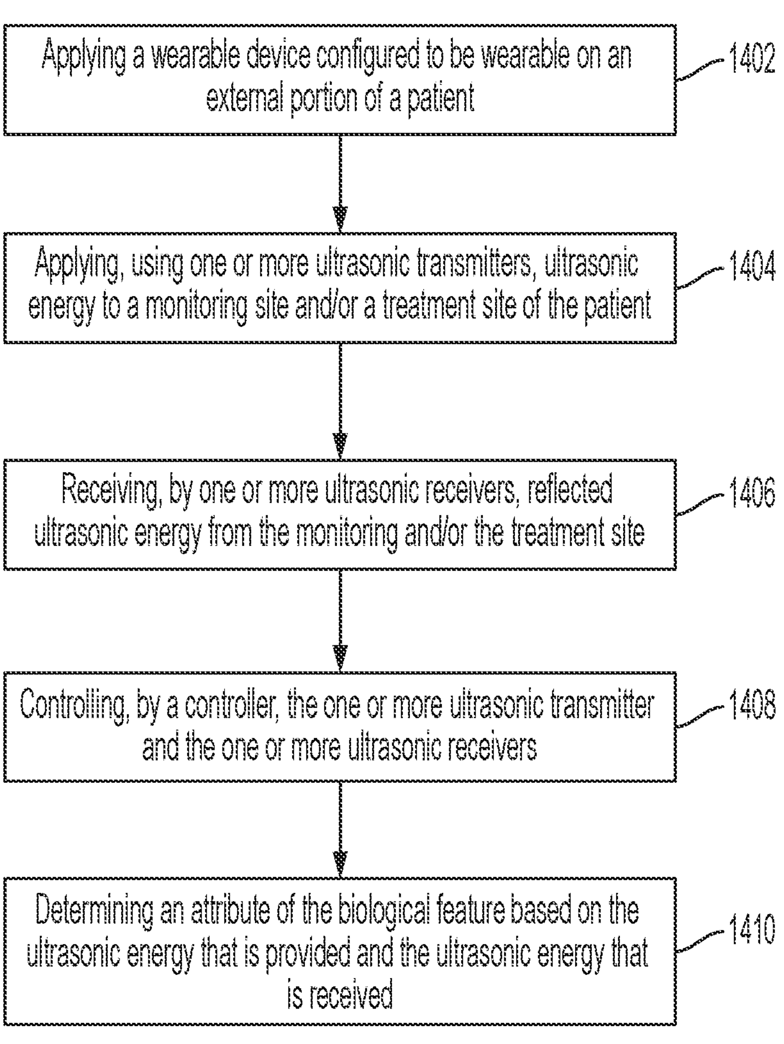

FIG. 14 shows a method for patient monitoring and/or treatment 1400 according to examples of the present disclosure. The method for patient monitoring and/or treatment 1400 comprises applying a wearable device, such as wearable device 600, configured to be wearable on an external portion of a patient, as in 1402. The wearable device, such as wearable device 600, is configured to monitor and/or treat a biological feature of the patient by applying, using one or more ultrasonic transmitters, ultrasonic energy to a monitoring site and/or a treatment site of the patient, as in 1404; receiving, by one or more ultrasonic receivers, reflected ultrasonic energy from the monitoring and/or the treatment site, as in 1406; and controlling, by a controller, the one or more ultrasonic transmitter and the one or more ultrasonic receivers, as in 1408, and determining an attribute of the biological feature based on the ultrasonic energy that is provided and the ultrasonic energy that is received, as in 1410.

In some examples, method 1400 can further comprise providing, by one or more stimulating electrodes, such as by using the transducer array (one or more transducers 602, therapeutic electrical stimulation to the monitoring site and/or the treatment site; recording, by one or more recording electrodes, neural activity at the monitoring site and/or the treatment site; and controlling, by the controller, the one or more stimulating electrodes and the one or more recording electrodes.

In some examples, method 1400 can further comprise providing power, by a power source, to the one or more ultrasonic transmitters, the one or more ultrasonic receivers, the one or more stimulating electrodes, the one or more recording electrodes, and the controller.

In some examples, method 1400 can further comprise controlling, by the controller, such as using control device 102, sensing device 116, and/or processor 402, at least one of the one or more ultrasonic transmitters, the one or more ultrasonic receivers, the one or more stimulating electrodes, the one or more recording electrodes based on a machine-learning algorithm.

In some examples, method 1400 can further comprise focusing, by one or more acoustic energy focusing elements, the ultrasonic energy at the monitoring site and/or treatment site.

In some examples, method 1400 can further comprise providing a signal, such as over communications interface 120, representative of the attribute of the biological feature to an implantable device or an external control device that applies a treatment based on the attribute of the biological feature.

In some examples, method 1400 can further comprise determining, such as using control device 102, sensing device 116, and/or processor 402, a heart rate based on the ultrasonic energy that is provided and the ultrasonic energy that is received.

In some examples, method 1400 can further comprise displaying the blood pressure and/or the heart rate on a user display of the wearable device, such as wearable device 600 and/or wristwatch 700.

In some examples, method 1400 can further comprise communicating, using a communications interface, such as communications interface 120, signals to/from a separate control device.

In some examples, method 1400 can further comprise receiving signals from the separate control device, such as over communications interface 120, to control when to take measurements of the biological feature.

In some examples, method 1400 can further comprise providing an inflating and/or a deflating signal, such as over communications interface 120, to an inflatable member, such as bladder 610, to allow for a release of moisture, oil, or ultrasound gel from the monitoring site and/or the treatment site.

In some examples, method 1400 can further comprise receiving and/or providing signals, such as by using communications interface 120, to one or more electromyography sensors, one or more accelerometry sensors, or both.

While the foregoing disclosure has been described in some detail by way of illustration and example for purposes of clarity and understanding, it will be clear to one of ordinary skill in the art from a reading of this disclosure that various changes in form and detail can be made without departing from the true scope of the disclosure and may be practiced within the scope of the appended claims. For example, all the methods, devices, systems, computer readable media, and/or component parts or other aspects thereof can be used in various combinations. All patents, patent applications, websites, other publications or documents, and the like cited herein are incorporated by reference in their entirety for all purposes to the same extent as if each individual item were specifically and individually indicated to be so incorporated by reference.

What is claimed is:

1. A patient monitoring and/or treatment system comprising:
- a wearable device configured to be wearable on an external portion of a patient, the wearable device configured to monitor and/or treat a plurality of biological features of the patient, the wearable device comprising:
  - one or more ultrasonic transmitters that provide ultrasonic energy to a monitoring site and/or a treatment site of the patient;
  - one or more ultrasonic receivers that receive reflected ultrasonic energy from the monitoring site and/or the treatment site;
  - one or more stimulating electrodes that provide therapeutic electrical stimulation to the monitoring site and/or the treatment site;
  - one or more recording electrodes that provide recording of neural activity at the monitoring site and/or the treatment site; and a controller that controls the one or more ultrasonic transmitters, the one or more ultrasonic receivers, the one or more stimulating electrodes, and the one or more recording electrodes, wherein the controller determines an attribute of the plurality of biological features based on the ultrasonic energy that is provided and the ultrasonic energy that is received and provides a signal representative of the attribute to the one or more stimulating electrodes of an implantable device or an external control device that applies a treatment based on the attribute of the biological feature.

2. The patient monitoring and/or treatment system of claim 1, wherein one of the plurality of biological features comprise a blood pressure, a tissue temperature, a tissue elasticity, or a volume of a target organ.

3. The patient monitoring and/or treatment system of claim 2, wherein the target organ is a bladder, a liver, or a brain.

4. The patient monitoring and/or treatment system of claim 2, wherein the wearable device further comprises one or more acoustic energy focusing elements that focuses the ultrasonic energy at the monitoring site and/or the treatment site.

5. The patient monitoring and/or treatment system of claim 1, wherein the attribute is determined based on a difference in arrival times between the ultrasonic energy that is provided and the reflected ultrasonic energy or received ultrasonic energy.

6. The patient monitoring and/or treatment system of claim 1, wherein the controller further determines a heart rate based on the ultrasonic energy that is provided and the ultrasonic energy that is received.

7. The patient monitoring and/or treatment system of claim 1, wherein the wearable device is incorporated into a wristwatch, a torniquet, a clothing, an undergarment, an arm sleeve, or a textile.

8. The patient monitoring and/or treatment system of claim 1, wherein the wearable device further comprises an inflatable member to allows for a release of moisture, oil, or ultrasound gel from the monitoring site and/or the treatment site.

9. The patient monitoring and/or treatment system of claim 1, wherein the wearable device further comprises a photoacoustic transceiver that provides light pulses to the monitoring site and/or the treatment site and receives ultrasound energy from the monitoring site and/or the treatment site.

10. The patient monitoring and/or treatment system of claim 1, wherein the wearable device further comprises a photothermal transmitter and a thermal camera, wherein the photothermal transmitter provides light pulses to the monitoring site and/or the treatment site and the thermal camera detects thermal changes at the monitoring site and/or the treatment site.

11. The patient monitoring and/or treatment system of claim 1, wherein the controller comprises a computer-readable medium that stores a trained machine-learning model that is programmed to predict one or more optimal interventions to be included in the treatment.

12. A method for patient monitoring and/or treatment comprising:

applying a wearable device configured to be wearable on an external portion of a patient, the wearable device configured to monitor and/or treat a biological feature of the patient by applying, using one or more ultrasonic transmitters, ultrasonic energy to a monitoring site and/or a treatment site of the patient;

receiving, by one or more ultrasonic receivers, reflected ultrasonic energy from the monitoring and/or the treatment site;

providing, by one or more stimulating electrodes, therapeutic electrical stimulation to the monitoring site and/or the treatment site;

recording, by one or more recording electrodes, neural activity at the monitoring site and/or the treatment site;

providing a signal representative of an attribute of the biological feature of a plurality of biological features to the one or more stimulating electrodes of an implantable device or an external control device that applies a treatment based on the attribute of the biological feature; and controlling, by a controller, the one or more ultrasonic transmitters, the one or more ultrasonic receivers, the one or more stimulating electrodes, and the one or more recording electrodes and determining the attribute of the biological feature based on the ultrasonic energy that is provided and the ultrasonic energy that is received and determining and applying the treatment based on the attribute of the biological feature.

13. The method for patient monitoring and/or treatment of claim 12, wherein one of the plurality of biological features comprise a blood pressure, a tissue temperature, a tissue elasticity, or a volume of a target organ.

14. The method for patient monitoring and/or treatment of claim 13, wherein the target organ is a bladder, a liver, or a brain.

15. The method for patient monitoring and/or treatment of claim 12, further comprising focusing, by one or more acoustic energy focusing elements, the ultrasonic energy at the monitoring site and/or treatment site.

16. The method for patient monitoring and/or treatment of claim 12, wherein the attribute of the biological feature is determined based on a difference in arrival times between the ultrasonic energy that is provided and the reflected ultrasonic energy or received ultrasonic energy.

17. The method for patient monitoring and/or treatment of claim 12, further comprising determining a heart rate based on the ultrasonic energy that is provided and the ultrasonic energy that is received.

18. The method for patient monitoring and/or treatment of claim 12, wherein the wearable device is incorporated into a wristwatch, a torniquet, a clothing, an undergarment, or a textile.

19. The method for patient monitoring and/or treatment of claim 12, further comprising providing an inflating and/or a deflating signal to an inflatable member to allow for a release of moisture, oil, or ultrasound gel from the monitoring site and/or the treatment site.

20. The method for patient monitoring and/or treatment of claim 12, wherein the controller comprises a computer-readable medium that stores a trained machine-learning model that is programmed to predict one or more optimal interventions to be included in the treatment.

* * * * *